US006069125A

United States Patent [19]

Pesaro

[11] Patent Number: 6,069,125

[45] Date of Patent: May 30, 2000

[54] NITRILE

[75] Inventor: Mario Pesaro, Zürich, Switzerland

[73] Assignee: Givaudan Roure (International) SA, Vernier-Geneve, Switzerland

[21] Appl. No.: 09/051,439

[22] PCT Filed: Oct. 24, 1996

[86] PCT No.: PCT/CH96/00377

§ 371 Date: Apr. 14, 1998

§ 102(e) Date: Apr. 14, 1998

[87] PCT Pub. No.: WO97/16512

PCT Pub. Date: May 9, 1997

[30] Foreign Application Priority Data

Nov. 1, 1995 [CH] Switzerland ............................ 3093/95

[51] Int. Cl.[7] ........................... A61K 7/46; C07C 255/00; A61L 9/00; C11D 3/50; C11D 9/44

[52] U.S. Cl. ................................ 512/10; 512/8; 558/388; 424/76.1; 510/102

[58] Field of Search .......................... 512/8, 10; 558/388; 424/76.1; 510/102

[56] References Cited

U.S. PATENT DOCUMENTS 3,408,396 10/1968 Suh et al. ................................ 564/171

OTHER PUBLICATIONS

D.E. Whyte, et al. *JACS.,* 65 (1943):1999–2000.

S.F. Birch, et al. *J. Chem. Soc.,* 123 (1923):2442–2446.

*Primary Examiner*—Cynthia Harris Kelly
*Assistant Examiner*—Monique T. Cole
*Attorney, Agent, or Firm*—Mark E. Waddell; Stephen M. Haracz; Bryan Cave LLP

[57] ABSTRACT

The invention relates to the use of cyclohexylidene phenyl acetonitrile as an odoriferous substance.

18 Claims, No Drawings

NITRILE

BACKGROUND OF THE INVENTION

Cyclohex-1-en-yl-phenylacetonitrile $C_6H_5CH(CN)—C_6H_9$ is described by V. J. Harding and W. N. Haworth in J.Chem.Soc. (1910), 486–498, as the product of the alkaline condensation of phenylacetonitrile and cyclohexanone.

However, it later emerged that the reaction product is in fact and reality cyclohexylidene-phenylacetonitrile $C_6H_5C(CN)=C_6H_{10}$ (I), D. E. Whyte, A. Cope, JACS 65 (1943), 1999–2000 and S. F. Birch, G. A. R. Kon, J. Chem. Soc. 123 (1923), 2442–2446.

Harding and Haworth describe the product obtained by them simply as a colourless oil having a pleasant ethereal odour. The later authors do not provide any information concerning this.

It is surprising that an odorant having extremely valuable properties and—as enlarged upon below—diverse use potentials is hidden behind this cursory, moreover extremely imprecise, non-specific olfactory description.

SUMMARY OF THE INVENTION

The invention is accordingly concerned with the compound I as an odorant, odorant compositions containing I and the use of I as an odorant.

The odour of I can be characterized as flowery-rosy, green, metallic, reminiscent of geranium.

On the basis of olfactory investigations it has furthermore been shown that I, especially having regard to its rose and geranium notes, is surprisingly outstandingly suitable as a replacement for rosacetol.

DETAILED DESCRIPTION OF THE INVENTION

Rosacetol (trichloro-methyl-phenyl-carbinyl acetate) is a much esteemed odorant because of its rose and geranium notes, but recently its use has declined more and more for ecological reasons (chlorine content).

It has also emerged that (I) is extraordinarily stable to acid and alkali and that (I) is distinguished by excellent substantivity. I is even quite clearly superior to roseacetol with respect to substantivity. The same is true for long-lastingness.

Under substantivity there is to be understood the adhesion of an odorant, e.g. to textiles, skin and hair after a washing operation.

Therefore, I is outstandingly suitable for use in the washing agent industry, e.g. as an odorant in detergents, conditioners, etc., as well as also as an odorant in cosmetics, e.g. in shampoos, soaps etc., especially as a replacement for rosacetol.

Having regard to the aforementioned valuable olfactory properties, compound I is suitable as an odorant, especially in combination with the extensive range of natural and synthetic odorants currently available on the market, for the creation of perfume compositions which can be used in all conventional fields of application. Examples of the numerous known odorant ingredients of natural or synthetic origin, whereby the range of the natural raw materials can embrace not only readily-volatile but also moderately-volatile and difficultly-volatile components and that of the synthetics can embrace representatives from quite a few classes of substance, are:

Natural products, such as oak moss absolute, basil oil, tropical fruit oils (such as bergamot oil, mandarine oil, etc.), mastix absolute, myrtle oil, palmarosa oil, patchouli oil, petitgrain oil, wormwood oil, lavender oil, rose oil, jasmin oil, ylang-ylang oil, sandalwood oil, alcohols, such as farnesol, geraniol, linalool, nerol, phenylethyl lcohol, rhodinol, cinnamic alcohol, cis-3-hexenol, menthol, α-terpineol, Sandela (3-isocamphyl-(5)-cyclohexanol), aldehydes, such as citral, α-hexylcinnamaldehyde, hydroxycitronellal, Lilial® (p-tert.butyl-α-methyl-dihydrocinnamaldehyde), methylnonylacetaldehyde, phenylacetaldehyde, anisaldehyde, vanillin, ketones, such as allylionone, α-ionone, β-ionone, isoraldein (isomethyl-α-ionone), verbenone, nootkaton, geranylacetone, esters, such as allyl phenoxyacetate, benzyl salicylate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate, methyl dihydrojasmonate, styrallyl acetate, vetiveryl acetate, benzyl acetate, cis-3-hexenyl salicylate, geranyl acetate, etc.

lactones, such as γ-undecalactone, δ-decalactone, pentadecan-15-olide, various components often used in perfumery, such as indole, p-methane-8-thiol-3-one, methyleugenol, eugenol, anethol, etc.

The odorant compositions manufactured using compounds I, especially those of flowery, flowery-spicy, flowery-fruity and flowery-oriental direction, captivate especially by their originality.

When used as an odorant, the compound I can be employed in wide limits which can range in compositions, for example, from about 0.1 (detergents) to about 30 weight percent (alcoholic solutions), without these values being, however, limiting values, since the experienced perfumer can also achieve effects with even lower concentrations or can synthesize novel complexes with even higher dosages. The preferred concentrations vary between about 1 and about 20 weight percent. The compositions manufactured with compounds I can be used for all kinds of perfumed consumer goods (eaux de Cologne, eau de toilette, extracts, lotions, creams, shampoos, soaps, salves, powders, deodorants, detergents, textile improvers, bleaching agents, textile conditioners, etc.

The compound I can accordingly be used in the manufacture of compositions and—as the above compilation shows—a broad range of known odorants or odorant mixtures can be used. In the manufacture of such compositions the odorants or odorant mixtures enumerated above can be used according to methods known to the perfumer, as follows e.g. from W. A. Poucher, Perfumes, Cosmetics and Soaps 2, 7th edition, Chapman and Hall, London, 1974.

EXAMPLE 1

Chypre composition

| | Parts by weight |
|---|---|
| Benzyl salicylate | 100 |
| Musk ambrette | 100 |
| Hydroxycitronellal | 100 |
| Sandela ® Givaudan | 100 |

-continued

| Chypre composition | Parts by weight |
|---|---|
| Vetivenyl acetate | 50 |
| Patchouli oil | 50 |
| Ylang-ylang oil | 40 |
| Methylnonylacetaldehyde 10% in propylene glycol | 40 |
| Galbanum oil 10% in alcohol | 40 |
| Balm oil | 30 |
| Oak moss absolute | 30 |
| Styrallyl acetate | 30 |
| Cinnamic alcohol | 20 |
| C-11 Aldehyde (10-undecenal) 10% in propylene glycol | 20 |
| Vernaldehyde | 20 |
| Eugenol extra | 20 |
| Marjoram oil | 10 |
| Frankinsence resinoid | 10 |
| γ-Undecalactone 10% in propylene glycol | 10 |
| Heliotropin | 30 |
| Rhodinol extra | 50 |
| | 900 |

When 100 parts of I are added to this somewhat heavy chypre composition, then this is altered in a very pleasantly fresh manner in the direction of citrus. The composition now becomes much lighter and much more modern.

Even after 24 hours the composition is still much lighter, fresher; it is very suitable for men's colognes having a modern image.

EXAMPLE 2

| Perfumery composition in the direction of hyacinth | Parts by weight |
|---|---|
| Phenylethyl alcohol | 200 |
| Hydroxycitronellal | 100 |
| Cinnamic alcohol | 100 |
| Phenylethyl isobutyrate | 80 |
| Phenylpropyl alcohol | 60 |
| Benzyl aetate | 50 |
| Baccartol ® Giv (rose base on the basis of citronelle oil/acetone condensation product | 40 |
| Phenylethyl formate | 40 |
| Citronellol | 30 |
| Eugenol | 20 |
| Galbanum oil | 20 |
| Phenylacetaldehyde 10% in propylene glycol | 20 |
| Maltol 1% in propylene glycol | 20 |
| Hydratropaldehyde dimethyl acetate | 10 |
| Geranyl acetate | 10 |
| | 800 |

When 200 parts of I are added to this hyacinth base, then it immediately becomes much more typical in the direction of hyacinth. I combines advantageously with the components which form the green note in that it brings these out in a substantially softer manner.

EXAMPLE 3

| Perfumery composition in the direction of hawthorn | Parts by weight |
|---|---|
| Terpineol | 250 |
| α-Hexylcinnamaldehyde | 100 |
| Phenylethyl alcohol | 140 |
| Hydroxycitronellal | 100 |
| Anisaldehyde ex anethol | 60 |
| Heliotropin | 50 |
| Linalool | 40 |
| Benzyl acetate | 30 |
| Geraniol | 30 |
| Bergamot oil | 30 |
| α-Ionone | 20 |
| Musk ambrette | 20 |
| Citronellol | 10 |
| Ethylene brassylate | 10 |
| Methylacetophenone | 10 |
| Coumarin | 10 |
| Indole pure | 5 |
| Geranyl acetate | 5 |
| Phenylacetaldehyde | 5 |
| Civette absolute 10% in propylene glycol | 5 |
| Ylang-ylang oil | 10 |
| Isoeugenol | 5 |
| Phenylacetaldehyde dimethyl acetal | 5 |
| | 950 |

When 50 parts of I are added to this flowery-sweet composition, then its powdery note becomes veiled very well in a flowery-rosy variant. A pleasant lilac note emerges in an intensified manner. Moreover, a honey note comes into play and confers more diffusion to the base.

EXAMPLE 4

| Perfumery composition in the direction of gardenia | Parts by weight |
|---|---|
| Hydroxycitronellal | 120 |
| Benzyl acetate | 100 |
| Bergamot oil | 100 |
| α-Ionone | 100 |
| Neroli oil | 70 |
| Styrallyl acetate | 70 |
| Linalool | 70 |
| Heliotropin | 50 |
| Ylang-ylang oil | 50 |
| Musk ketone (4-tert.butyl-3,5-dinitro-2,6-dimethyl-acetophenone) | 50 |
| Isoeugenol | 30 |
| Jasmine oil | 30 |
| α-Hexylcinnamaldehyde | 30 |
| Musk ambrette | 30 |
| Phenylacetaldehyde 50% in propylene glycol | 15 |
| Civette absolute 10% in propylene glycol | 5 |
| C-10 Aldehyde (n-decyl-) 10% in propylene glycol | 5 |
| Orange oil Californian | 5 |
| | 930 |

When 70 parts of I are added to this flowery base in the direction of gardenia, then this takes on an intensified honey note, which makes the base more rounded-off. The base becomes much more harmonic by the presence of I. I forms a decidedly compensatory factor in the composition.

I claim:

1. A perfumed article selected from eaux de Cologne, eau de toilette, extracts, lotions, creams, shampoos, soaps, salves, powders, cosmetics, deodorants, detergents, textile improvers, bleaching agents, and textile conditioners which contains an olfactorily-effective amount of cyclohexylidene-phenylacetonitrile.

2. The perfume article of claim 1 which is in the form of an eaux de Cologne.

3. The perfume article of claim 1 which is in the form of an eau de toilette.

4. The perfume article of claim 1 which is in the form of a cosmetic.

5. The perfume article of claim 1 which is in the form of a detergent.

6. The perfumed article of claim 1 wherein the article has a note selected from rose notes, geranium notes, and a combination thereof.

7. The perfumed article of claim 1 which contains from about 0.1 weight percent to about 30 weight percent of cyclohexylidene-phenylacetonitrile.

8. The perfumed article of claim 6 which contains from about 1 weight percent to about 20 weight percent of cyclohexylidene-phenylacetonitrile.

9. The perfumed article of claim 1 which is stable to alkali and acid.

10. A method of imparting a rose note, a geranium note or a combination thereof to a perfumed article comprising adding to the perfumed article an olfactorily-effective amount of cyclohexylidene-phenylacetonitrile.

11. The method of claim 10 wherein the perfumed article is selected from eaux de Cologne, eau de toilette, extracts, lotions, creams, shampoos, soaps, salves, powders, cosmetics, deodorants, detergents, textile improvers, bleaching agents, and textile conditioners.

12. The method of claim 10 wherein from about 0.1 weight percent to about 30 weight percent of cyclohexylidene-phenylacetonitrile is added to the perfumed article.

13. The method of claim 12 wherein from about 0.1 weight percent to about 30 weight percent of cyclohexylidene-phenylacetonitrile is added to the perfumed article.

14. The method of claim 11 wherein the perfumed article is eaux de Cologne.

15. The method of claim 11 wherein the perfumed article is eau de toilette.

16. The method of claim 11 wherein the perfumed article is a cosmetic.

17. The method of claim 11 wherein the perfumed article is detergent.

18. The method of claim 10 wherein the perfumed article is stable to alkali and acid.

* * * * *